United States Patent
Ventosa Rull et al.

(10) Patent No.: US 8,613,953 B2
(45) Date of Patent: Dec. 24, 2013

(54) METHOD FOR OBTAINING SOLID MICRO- OR NANOPARTICLES

(75) Inventors: Nora Ventosa Rull, Bellaterra (ES);
Jaume Veciana Miró, Bellaterra (ES);
Mary Cano Sarabia, Bellaterra (ES);
Santiago Sala Vergés, Bellaterra (ES)

(73) Assignees: Consejo Superior de Investigaciones Científicas (ES); Centro de Investigación Biomédica en Red en Bioingeniería, Biomateriales Y Nanomedicina (ES)

( * ) Notice: Subject to any disclaimer, the term of this patent is extended or adjusted under 35 U.S.C. 154(b) by 0 days.

(21) Appl. No.: 13/142,764

(22) PCT Filed: Nov. 6, 2009

(86) PCT No.: PCT/ES2009/070485
§ 371 (c)(1),
(2), (4) Date: Sep. 20, 2011

(87) PCT Pub. No.: WO2010/076360
PCT Pub. Date: Jul. 8, 2010

(65) Prior Publication Data
US 2012/0004308 A1 Jan. 5, 2012

(30) Foreign Application Priority Data
Dec. 30, 2008 (ES) .................. 200803753

(51) Int. Cl.
*A61K 9/14* (2006.01)
*B29B 9/00* (2006.01)

(52) U.S. Cl.
USPC ........... 424/489; 977/778; 977/786; 977/788; 977/795; 977/836; 977/903; 977/904; 977/906; 977/915; 977/773; 514/951; 264/5

(58) Field of Classification Search
USPC ......... 977/773, 778, 786, 788, 795, 836, 903, 977/904, 906, 915; 424/489; 264/5
See application file for complete search history.

(56) References Cited

U.S. PATENT DOCUMENTS

| | | | | |
|---|---|---|---|---|
| 6,461,642 B1 * | 10/2002 | Bisrat et al. | ................... | 424/489 |
| 7,276,190 B2 * | 10/2007 | Reverchon | ........................ | 264/5 |
| 7,291,295 B2 * | 11/2007 | Ventosa Rull et al. | ............ | 264/5 |

(Continued)

FOREIGN PATENT DOCUMENTS

| | | |
|---|---|---|
| ES | 2170008 | 7/2002 |
| ES | 2228149 | 1/2005 |

(Continued)

OTHER PUBLICATIONS

PCT International Search Report/Written Opinion for PCT/ES2009/070485, completed Jan. 25, 2010.

*Primary Examiner* — Jane C Oswecki
(74) *Attorney, Agent, or Firm* — Barnes & Thornburg LLP

(57) ABSTRACT

The invention provides a novel method for obtaining solid micro- or nanoparticles with a homogeneous structure. A method is provided for obtaining solid micro- or nanoparticles with a homogeneous structure having a particle size of less than 10 μm where the processed solid compound has the natural, crystalline, amorphous, polymorphic and other features associated with the starting compound. In accordance with the invention a method which also makes it possible to obtain solid micro- or nanoparticles with a substantially spheroidal morphology is provided.

17 Claims, 8 Drawing Sheets

(56) References Cited

U.S. PATENT DOCUMENTS

Figure 1:
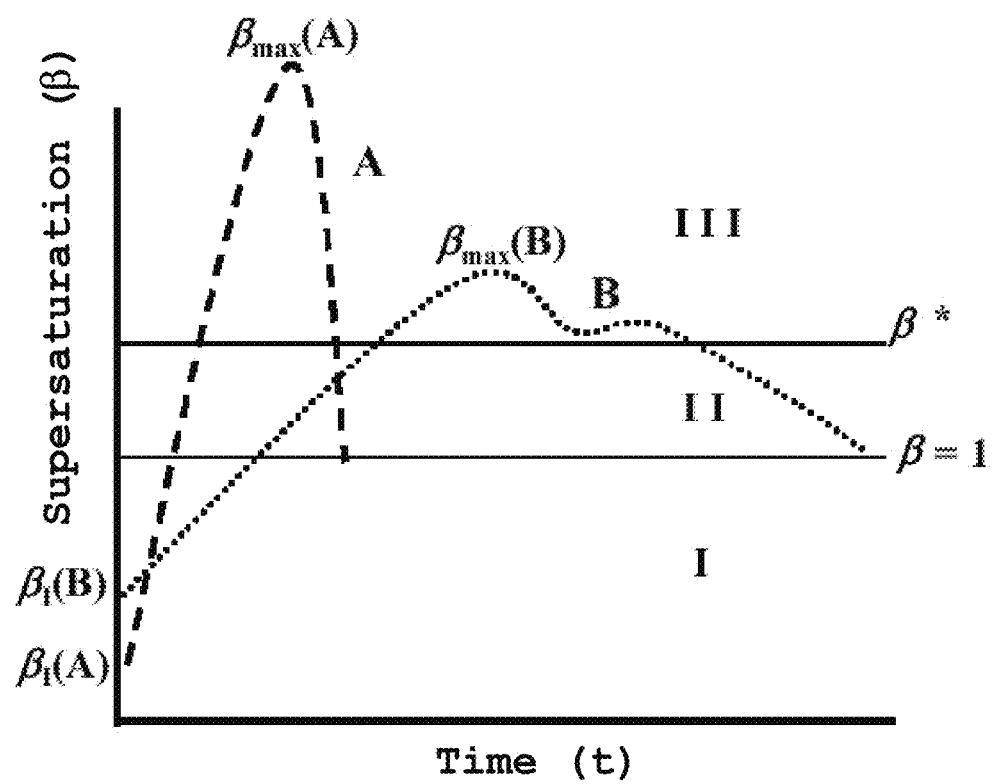

| | | | |
|---|---|---|---|
| 2001/0055561 A1* | 12/2001 | Saim et al. | 423/658.5 |
| 2003/0098517 A1 | 5/2003 | Rull et al. | |
| 2004/0178529 A1 | 9/2004 | Reverchon | |
| 2007/0259971 A1* | 11/2007 | Ventosa et al. | 516/198 |
| 2011/0021592 A1* | 1/2011 | Magdassi et al. | 514/406 |

FOREIGN PATENT DOCUMENTS

| | | |
|---|---|---|
| ES | 2261469 | 11/2006 |
| ES | 2265262 | 1/2007 |
| ES | 2292300 | 1/2008 |
| WO | WO03/004142 | 1/2003 |

* cited by examiner

METHOD FOR OBTAINING SOLID MICRO- OR NANOPARTICLES

CROSS-REFERENCE TO RELATED APPLICATIONS

This application is a U.S. national counterpart application, filed under 35 U.S.C. §371, of International Application Serial No. PCT/ES2009/070485 filed Nov. 6, 2009, which claims priority to Spanish Patent Application Serial No. P200803753 filed Dec. 30, 2008. The disclosures of both of which applications are hereby incorporated herein by reference in their entirety.

BACKGROUND OF THE INVENTION

1. Field of the Invention

This invention provides a process to obtain solid micro- or nanoparticles with a homogenous structure from a microemulsion.

According to the invention, it provides a process which allows to obtain solid micro- or nanoparticles of a homogenous structure, with a size of a particles of less than 10 µm in which the solid processed compound reveals the nature, e.g., crystalline, amorphous, polymorphic, etc. . . . , typical of the original compound. According to the invention process, sizes as small as 500 nm can be obtained. Advantageously, the invention provides a process to obtain for obtaining solid micro- or nanoparticles with an aspect ratio close to the unity (1), i.e., with a substantially spheroidal morphology.

2. Description of Related Art

There are in the state of the art different processes that refer to obtaining particles finely divided as a strategy to increase their water solubility and, therefore, the bioavailability of active molecules in physiological conditions. Some of these processes have used as a model molecule, ibuprofen to show their effectiveness in this way. Below, are some details of the work based on experiments with ibuprofen.

The article by N. Rasenack, B. W. Müller, Pharmaceutical Research, 2002, 19, 1894-1900, proposes the use of a technique called in-situ Micronization as an alternative to the conventional techniques of micronization by grinding to obtain micro- and nanoparticles of solids slightly insoluble in water such as ibuprofen. To form the particulate solid an aqueous solution is poured in a stabilizing agent over a solution of ibuprofen in an organic solvent miscible in water. In this process water acts as a non-solvent of the product causing its precipitation and producing a suspension of it. This precipitation is followed by a process of "spray drying" to eliminate the liquid from said suspension and isolating the particulate solid. This solid consists of microparticles of the active principle coated with the stabilizing agent.

In the article by M. Charoenchaitrakool, F. Deghani, N. R. Foster, Ind. Eng. Chem. Res. 2000, 39, 4794-4802 racemic ibuprofen and S-ibuprofen have been micronized by the RESS process described in U.S. Pat. No. 4,582,731. This process consists in the depressurization of a solution of a product (ibuprofen) in a supercritical fluid ($CO_2$) through a nozzle, causing its precipitation. Microparticles of the product (1-15 µm) are obtained with an irregular geometry and with a considerable loss in crystallinity.

In the article by D. Hermsdorf, Stephan Jauer, R. Signorell, Molecular Physics, 2007, 105, 8, 951-959, racemic ibuprofen and S-ibuprofen have also been micronized using the process RESS. Particles of pure ibuprofen strongly agglomerated and coagulated which consist of primary particles of 100-500 nm with irregular shapes.

The article by P. Pathak, M. J. Meziani, T. Desai, Y.-p. Sun, J. Supercrit. Fluids, 2006, 37, 279-286 describes how to obtain suspensions in water of not-agglomerated ibuprofen particles at a nanometric scale by using the RESOLV process. This process consists in depressurizing the RESS method over an aqueous solution obtaining the stabilization of particles in the aqueous medium which can contain a surfactant. This process is described in patent applications WO9965469 and WO9714407.

However, it is often desirable to obtain solid particles finely divided with a greater control of the particle size.

Mainly, three methodologies have been developed to prepare finely divided solid particles based on the use of emulsions and $CO_2$.

In the first methodology, the synthesis of the particles is done by an anti-solvent effect of the $CO_2$ ("anti-solvent gas", GAS) over an emulsion of the solute to be precipitated. This methodology has been developed by Zhang et al., and comprises two stages: In the first stage, an emulsion of water in a non-polar solvent (usually iso-octane) is prepared which contains the solute to be precipitated and a surfactant, both dissolved. The second stage consists in the precipitation of the particles when the emulsion comes into contact with the $CO_2$. This methodology is described, e.g., J. Zhang, B. Han, X. Zhang, J. He, Z. Liu, T. Jiang, G. Yang, Chem. Eur. J. 2002, 8, 17, 3879.

The second methodology, called "supercritical fluid extraction emulsion" (SFEE), is based in the precipitation of particles from the extraction by $CO_2$ of the non-polar solvent which is a part of the emulsion. This methodology has been developed by "Ferro Corporation" (US2004071781). In this process, the synthesis of the particles also comprises two stages. In the first one, called preparation of the emulsion, the solute to be precipitated is dissolved in a non-polar saturated solvent with water. On the other hand, the surfactant is dissolved in saturated water with the same non-polar solvent. Next, both solutions are mixed to form an emulsion. Finally, the resulting emulsion is homogenized in a homogenizer. In the second stage, the precipitation of the particles takes place. The emulsion is pulverized through a nozzle in an extraction column through which $CO_2$ circulates in a counter-current flow. The emulsion droplets come into contact with the $CO_2$, and it extracts the non-polar solvent from the emulsion. The particles will precipitate into fine particles suspended in the aqueous phase. Therefore, through this technology the precipitation of the particles takes place by the extracting effect of the non-polar solvent which causes the precipitation. Within this methodology, based on the extracting role of $CO_2$, Inserm Inst Nat Sante & Rech Medicale (WO2007072106) a new process has been developed to prepare the particles. This process is based in the extraction of the organic solvent of the emulsion by the $CO_2$, upon changing it from critical conditions to a liquid state. The particles' synthesis comprises the preparation of an emulsion, and the solidification of the discontinuous phase to form the particles. The emulsion will be made up by a compressed fluid (continuous phase), and a solvent which will contain the solute to be precipitated dissolved (discontinuous phase). The compressed fluid will extract the solvent from the discontinuous phase, upon changing from critical conditions to liquid state, therefore precipitating the particles.

The third particle precipitation methodology is based on the use of emulsions made up of water as a discontinuous medium and $CO_2$ as the continuous medium ("water-in-$CO_2$ emulsions"). In this methodology there can be two types of different precipitations. In the first place, there is the one developed by "Ferro Corporation" (WO2004110603) which is based in the pulverization of an emulsion made up of water and $CO_2$ within a reactor, and a later elimination of the solvents so as to finally obtain the particles. The synthesis comprises three stages. In the first one, an emulsion is prepared. The continuous phase will be made up by compressed fluid or supercritical ($CO_2$), and the discontinuous phase by a solution (preferably aqueous) of the solute to be precipitated and/or reacted. In a second stage, the emulsion is pulverized through a nozzle forming small droplets of emulsion. In a third stage, the compressed fluid and the organic solvent from the droplets is eliminated which leads to the precipitation of the particles. In second place is the use of emulsions made up of water as a discontinuous medium and $CO_2$ as the continuous medium. In this case, the method of precipitation is based in the precipitation of the particles from a mixture of two emulsions water/$CO_2$. The synthesis of the particles comprises two stages: In a first stage two emulsions are prepared. The continuous phase is made up of compressed fluid or supercritical ($CO_2$), and the discontinuous phase by the solution (preferable aqueous) of the solute to be precipitated and/or reacted. In a second stage, the two emulsions are mixed and their components react precipitating the particles. The article by C. A. Fernandez, C. M. Wai, Small 2006, 2, 11, 1266, describes how to obtain the silver nanoparticles through this methodology.

However, in many occasions it is desirable to obtain solid micro- or nanoparticles with a high homogeneity in the size of the particle and with a greater control of it. Besides, in most existing techniques to date the nature of the initial product does not manifest in the same way in the final processed product, loosing or reducing, e.g., their crystalline nature in the final product.

Therefore, there isn't yet a technology which allows to reduce the size of the particle which allows a greater control and homogeneity of it and which at the same time allows the very own properties, e.g., crystalline, of the nature of the initial product to manifest in the solid micro- or nanoparticles obtained after processing.

BRIEF SUMMARY OF THE INVENTION

To said purpose, this invention provides a process to obtain solid micro- or nanoparticles from a microemulsion. The microemulsions are characterized in that they are thermodynamically stable; they form spontaneously with the average diameter of the nanometric droplets and by being transparent or bluish translucent.

The process to obtain the solid micro- or nanoparticles is based on providing a microemulsion which includes water ($H_2O$), an organic solvent or a mixture of organic solvents, a solid compound C and a fluid compound B, where said micro- or nanoparticles obtained posses a homogenous structure with a particle size that can reach values as low as 500 nm. According to the invention, the precipitation of the solid micro- or nanoparticles is done by the anti-solvent effect of water without requiring a highly effective agitation system. The process of the invention allows to directly obtain micro- or nanoparticles of a homogenous structure, which manifest the very own properties of the nature of the initial product, e.g., crystallinity, amorphousness, polymorphism, etc. . . . , in the processed product and optionally have an aspect ratio close to the unity (1), i.e., have a substantially spheroidal morphology, and size of particle comprised between 10 µm and 500 nm.

A first aspect of this invention is to provide a new process to obtain solid micro- or nanoparticles of a homogenous structure. Said process comprises preparing a mixture which includes an organic solvent or a mixture of organic solvents, a solid compound C and water ($H_2O$), and obtain a microemulsion by adding a fluid B, and increasing the pressure until reaching a first pressure ($P_1$) where the predetermined supersaturation value (β) of the solid compound C is lower or equal to 1. Next, a variation of said first pressure ($P_1$) to a second pressure ($P_2$) allows to modify the solvent effect of water ($H_2O$) in said first pressure ($P_1$) to an anti-solvent in said second pressure ($P_2$) which causes the precipitation of solid micro- or nanoparticles of a homogenous structure; Next, they can be isolated and collected at said second pressure ($P_2$) said solid micro- or nanoparticles using conventional methods.

Advantageously, with the process according to the first aspect of the invention micro- or nanoparticles with an improved stability are provided, i.e., with a lower risk of degradation or structural change during their storage, less reactivity and greater stability to mechanical or thermal stress, besides a lower sensibility to humidity.

A second aspect of this invention is the use of said improved micro- or nanoparticles in a composition which also comprises other acceptable pharmaceutical excipients. Advantageously, according to the process other the invention solid micro- or nanoparticles of a homogenous structure, crystalline and with an aspect ratio close to the unity can be obtained, i.e., of a spheroidal morphology, which makes them useful to applications where the structure and morphology of the particles has a decisive influence for their administration.

A third aspect of this invention is the use of said micro- or nanoparticles of homogenous structure and with an aspect ratio close to the unity for the preparation of aerosols based on active principles of use via inhalation or for preparing suspensions of a therapeutically active principles which have low hydrosolubility and bioavailability.

BRIEF DESCRIPTION OF THE DRAWINGS

FIG. 1 shows two curves of supersaturation with regards to time (t), curve A and curve B;

FIG. 2 shows a facility to carry out the process of the invention;

FIG. 3 shows the variation in optic density observed in a microemulsion formed according with the process of the invention;

FIG. 4 represents a differential scanning calorimetry profile (DSC) of the solid compound C (ibuprofen) obtained according to the process of the invention, with or without a surfactant (PEG6000);

FIG. 5 represents an X-ray diffraction spectrum of solid compound C (ibuprofen) obtained using the process of the invention in presence or absence of surfactant (PEG6000);

FIG. 6A is an image of a scanning electron microscope (SEM) of the ibuprofen compound obtained without surfactant and $\Delta P<0$ ($P2<P1$);

FIG. 6B is an image of a scanning electron microscope (SEM) of the ibuprofen compound obtained with PEG6000 and $\Delta P<0$ ($P2<P1$); and FIG. 6C is an image of a scanning electron microscope (SEM) of the ibuprofen compound obtained with PEG6000 and $\Delta P>0$ ($P2>P1$).

DETAILED DESCRIPTION OF THE INVENTION

In this invention, "fluid B" refers to a fluid which at atmospheric pressure and room temperature is a gas and which at a first pressure ($P_1$), greater than atmospheric pressure, is miscible with the organic solvent, and immiscible or partially miscible with water. Preferably, said fluid B is selected from $CO_2$ and Freon. Besides, according to the pressure and temperature conditions according to the process of the invention said fluid B does not act as a supercritical fluid in any of the stages defined in the attached claims.

In this invention "organic solvent" refers to any polar or apolar organic solvent or mixture of both that is miscible with $CO_2$ at a first pressure ($P_1$), higher than the atmospheric pressure, and miscible with water at atmospheric pressure.

Preferably, said organic solvent can be selected from the group comprised by: monohydric alcohols such as methanol, ethanol, 1-propanol, 2-propanol, 1-butanol, 1-hexanol, 1-octanol and trifluoroethanol, polyhydric alcohols such as propylene glycol, PEG 400, and 1,3-propanediol; ethers such as tetrahydrofuran (THF), and diethyl ether, alkanes such as decalin, isooctane, and mineral oil; aromatics such as benzene, toluene, chlorobenzene, and pyridine, amides such as n-methylpyrrolidone (NMP), and N,N-dimethylformamide (DMF); esters such as ethyl acetate, propyl acetate, and methyl acetate, 1,2-dichloroethane, and 1,1,1-trichloroethane, ketones such as acetone, methyl ethyl ketone, and Methyl isobutyl ketone; other solvents such as ethylenediamine, acetonitrile, and trimethyl phosphate. Solvents with low volatility such as dimethylacetamide or dimethyl sulfoxide or an ionic liquid can also be used. In an embodiment of the present invention, the preferred organic solvent is acetone.

In this invention "surface active agents" or "surfactant" refers to an anionic, cationic or neutral agents which can be selected among an emulsifying agent, surface agent, stabilizing, protective colloid and, more preferably, from among, the polyethylene glycols (PEGs), the polysorbates, poloxamer, ascorbyl palmitate, lecithin, hexadecyltrimethylammonium bromide (CTAB), sulphates, sulfonates, phosphates, carboxylates, and sulfosuccinates. Yet more preferably, selected from among polyethylene glycols 6000 (PEG6000), bis(2-ethylhexyl) sodium sulfosuccinates (AOT), sodium dodecyl sulphate (SDS), Sodium octyl sulphate, sodium tetradecyl sulphate, octadecyl sodium sulphate, sodium laurate, cholesterol sulfate sodium salt, sodium dodecyl sulfonate, sodium decyl sulfonate, sodium octyl sulfonate, sodium oleate, as well as among others, or a mixture of thereof.

In this invention "aspect ratio" (RA) refers to a value close to 1, where said value has the sole purpose of defining a particle commonly called of a spheroidal morphology. The aspect ratio can be commonly defined as the relationship between the length and height of the particle, where the length is the greatest distance when measured between two points of the perimeter of the projection of the particle independent of its orientation and width is the greatest distance between two points contained in the intersection of one of the perpendicular axis to the length and perimeter according with the process defined in S. Almeida-Prieto, J. Blanco-Mendez, F. J. Otero-Espinar, European journal of Pharmaceutics and Biopharmaceutics 67 (2007) 766-776, particularly, page 772, FIG. 5, process (a), of Research paper "Microscopic image analysis techniques for the morphological characterization of pharmaceutical particles: influence of the software, and the factor algorithms used in the shape factor estimation" based on the determination of which the value of the aspect ration is indicated in this invention, without this meaning that other methods can not be used to define a particle with a spheroidal morphology.

In this invention "solid compound C" refers to a substance or mixture of solid substances, selected from a drug, explosive, colorant, pigment, cosmetic, polymer, catalyst, chemical product for the agriculture or other particle or substance completely insoluble in water, and susceptible to being dissolved at the pressure at which the value of supersaturation ($\beta$) is less than or equal to 1, where the temperature is within the margins described later according to the invention.

The formation of micro- or nanoparticles can be monitored and controlled by analysing the turbidity of the system, in turn induced by successive pressure changes and mole fraction of $CO_2$ ($X_{CO2}$) in the system. The turbidity of the system can be measured by optic density. The optic density (OD) is defined as the absorbance of an optic element at a determined wavelength in which the system does not absorb, and by unit of optical path or distance. The optical density is a property used in the invention to detect variations of the supersaturation value ($\beta$) in the system when $\beta \geq 1$, and of the supramolecular organization of its components. The "on-line" monitoring of the system is done by means of a UV visible Spectrophotometer.

According to the first aspect of this invention, a process is provided to obtain micro- or nanoparticles with a homogenous structure.

The process according to the first aspect of the invention comprises:
  a) preparing in a closed container a mixture that includes an organic solvent or a mixture of organic solvents, a solid compound C and water ($H_2O$),
where in said stage a) there is at least one liquid phase and one solid phase, characterized in that it also comprises:
  b) adding a fluid B to said mixture prepared in stage a) so that the pressure of the container is increased until to reach to a first pressure ($P_1$), allowing said addition of fluid B at said first pressure ($P_1$) to prepare a microemulsion of an organic phase saturated with water,
where there is no solid phase in this stage and where at said first pressure (P1) the value of the predetermined supersaturation ($\beta$) of the solid compound C is lower to or equal to 1,
  c) varying said first pressure ($P_1$) to a second pressure ($P_2$), where said variation in pressure is different from zero ($\Delta P \neq 0$), and where at said second pressure ($P_2$) said water ($H_2O$) has an anti-solvent effect which cause the precipitation of solid micro- or nanoparticles of compound C with homogenous structure;
where in said stage c) there are at least one liquid phase and one solid phase;
  and, if desired;
  d) collecting at said second pressure ($P_2$) said solid micro- or nanoparticles by conventional methods.

In said stages a), b) and c), the transition from one to another is determined by the phase changes observed through variations in the optic density.

Thus, en stages a) and c), the nature of the solvent will determine the existence of one or more liquid phases, depending on if it is a polar or non-polar organic solvent or mixtures of both or of more than one of them. In said stages a) and c) when a polar solvent is used there is a unique liquid phase. If a non-apolar solvent is used, there will be more than one liquid phases determined by optic density.

Advantageously, the mixture of stage a) is prepared at atmospheric pressure and room temperature. However, the temperature of the process, regardless of the stage, can be comprised between −50° C. and 200° C., and yet more preferably between 20° C. and 50° C.

Optionally, stages a) and b) can be carried out simultaneously. In this embodiment, where stages a) and b) are carried out simultaneously, the process continues to stage c). The increase in pressure of the container to the first pressure ($P_1$) in stage b) can be carried out whether by adding fluid B, the use of mechanical means such as, e.g., a piston inside the container, or by adding an inert gas, such as for example $N_2$.

Also, the pressure variation in stage c) to a second pressure ($P_2$) can be done in the same way.

In yet another embodiment of this invention, in stage a) a surfactant can also be added. Advantageously, the presence of the surfactant in the microemulsion obtained in stage b) improves the stability of the final dispersion even more, which is capable of favouring the control of the nucleation processes and crystalline growth, thus, obtaining still smaller particle sizes and narrower size distributions.

It is worth pointing out that in stage b), when said first pressure ($P_1$) is reached, the supersaturation value ($\beta$), i.e., the ratio between the concentration [C] of the solid compound C to the concentration of the supersaturation [$C_s$] of said solid compound C in the microemulsion:

$$\beta = [C]/[C_S] \leq 1$$

where said microemulsion is formed by said organic solvent or mixture of organic solvents, said water ($H_2O$) and said fluid B and, optionally, a surfactant.

The microemulsion formed in said stage b) comprises an organic phase saturated with water, where said organic phase is formed by said fluid B, said organic solvent or a mixture of organic solvents and said solid compound C and optionally, said surfactant.

The variation of the first pressure ($P_1$) to the second pressure ($P_2$), where said positive or negative pressure variation, i.e., increasing or decreasing the first pressure ($P_1$) to a second pressure ($P_2$), stimulates the precipitation of the solid micro- or nanoparticles of homogenous structure due to the anti-solvent effect of the water ($H_2O$) at said second pressure ($P_2$), where the supersaturation value ($\beta$) is greater than 1.

Surprisingly, the authors of this invention have found that the final characteristics of the micro- or nanoparticles obtained do not depend in the effectiveness of agitation as is the case in the technologies described to date, but rather the degree of homogenous distribution of water in the microemulsion obtained which after a variation in the pressure (stage c)) causes the water to act as an anti-solvent and causes the precipitation of the solid micro- or nanoparticles. Therefore, the process of this invention represents a considerable change in the line followed up to now for obtaining finely divided particles based mostly in that a higher agitation or homogenization of the solution that contains the solid to be precipitated provides a smaller sized particle.

According to the present invention, the anti-solvent effect of water in determined pressure conditions and in an adequate medium, a microemulsion, allows to obtain solid micro- or nanoparticles of a homogenous structure whose micro- or nanoparticles also manifest the initial properties of the nature of the organic compound to be precipitated.

In an embodiment of the invention, when the pressure variation in stage c) is positive, i.e. $\Delta P > 0$, the second pressure ($P_2$) is greater than the first pressure ($P_1$), and the precipitation is a reversible phenomenon.

In another embodiment of the invention, when the pressure variation in stage c) is negative, i.e. $\Delta P < 0$, the second pressure ($P_2$) is lower than the first pressure ($P_1$) and the precipitation is an irreversible phenomenon.

According to the process of the invention, when $\Delta P > 0$ the organic solvent can be selected from a polar or non-polar solvent and when $\Delta P < 0$ the organic solvent is a polar solvent.

Next, the micro- or nanoparticles are collected at said second pressure ($P_2$) by conventional means. Optionally, said particles can be isolated and collected, e.g., by filtration and also when $\Delta P < 0$ they can be collected over a water current so that a suspension of said particles is obtained. Said suspension has application in the preparation of a medicine preferably by oral, intravenous or mucosal administration.

With the pressure variation (stage c) of the microemulsion the behaviour of the water is modified, which goes from acting as a solvent at $P_1$ to acting as an anti-solvent at $P_2$ which causes the precipitation of the solid micro- or nanoparticles with a homogenous structure. In an embodiment of the invention, said solid micro- or nanoparticles are also crystalline. Also, in another embodiment of this invention said solid micro- or nanoparticles have an aspect ratio considerably equal to the unity (1).

Advantageously, with the process according to the first aspect of the invention micro- or nanoparticles are provided with an excellent aspect ratio-property. Thus, with the process of the invention micro- or nanoparticles with improved structural characteristics can be obtained such as, e.g., a greater crystallinity, which confers greater stability during storage, fluidity and less tendency to absorb humidity.

Furthermore, adding fluid B, for example $CO_2$ in the process of the invention and unlike those of the techniques described to date, does not cause the precipitation of the solid compound C in the form of finely divided particles.

With it, the process of the invention provides a new technology for obtaining solid micro- or nanoparticles where fluid B is not responsible for the precipitation, nor is it used in supercritical state in any stage of the process. It is believed that the anti-solvent effect of water at $P_2$ and the conditions in which the precipitation occurs favour a nucleation and growth of crystalline structure with a substantially spheroidal morphology. Thus, the new process provides unexpected properties to the micro- or nanoparticles obtained, properties not described in the state of the art at said micro- or nanoscale.

The crystallinity, and therefore, the absence of an amorphous solid in, e.g. a pharmaceutical product is of great importance because it is considered that formulas that contain amorphous forms are less stable than the crystalline solid and, therefore, carry a risk regarding its preservation of the properties of the material during storage. These partial or completely amorphous materials usually have greater reactivity and are unstable to mechanical and thermal stress and have a greater tendency to absorb water.

Furthermore, advantageously, according to the first aspect of this invention, a process for obtaining micro- or nanoparticles with a considerably spheroidal morphology, also called morphology with an aspect ratio close to 1, according to the method mentioned in the definitions section for aspect ratio.

Morphology is a highly determining property in the preparation and administration of, for example, a medicine which already has special effect in the properties of pharmaceutical formulation such as fluidity and compactness. Thus, the more regular and similar to the spherical form is the morphology of the particles the greater their fluidity in aerosol formulas, such as the ones used for oral administration.

The particles obtained have a narrow volumetric size distribution and an average associated sphere diameter of less than 10 μm, generally less than 1 μm. Advantageously, the size of the particle obtained with the process defined in the invention is comprised between 10 μm and 500 nm, preferably between 3 μm and 800 nm, more preferable between 1 μm and 700 nm.

Thus, according to the second aspect of the invention, the micro- or nanoparticles obtained according to the first aspect of the invention are of a great interest in the preparation of a composition which also comprises other acceptable pharmaceutical excipients where the structure and morphology of the micro- or nanoparticles is a determining factor for their application.

Also, according to the third aspect of the invention said micro- or nanoparticles obtained are of special interest in the preparation of an aerosol for inhaled administration of medicines destined to the treatment of pulmonary diseases, or of other formulas where the purpose is to increase the bioavailability of active substances with low water solubility.

FIG. 1 shows two curves of supersaturation with regards to time (t), curve A and curve B. Said FIG. 1 has three different areas, area I where there is no crystal growth, area II where there is crystal growth but no nucleation and area III where there is nucleation. Curve A corresponds to a qualitative profile of supersaturation corresponding to a process of crystallization where the nucleation phenomenon is favoured above the crystal growth process. Curve B corresponds to a qualitative profile of supersaturation of a process where the crystal growth is favoured above the nucleation.

The process of the invention follows a supersaturation type A curve, which is characterized in that it takes place in area IIII in a brief period of time and, therefore, there is a high nucleation, with translates into a greater number of solid particles with a smaller size.

Figure 2:
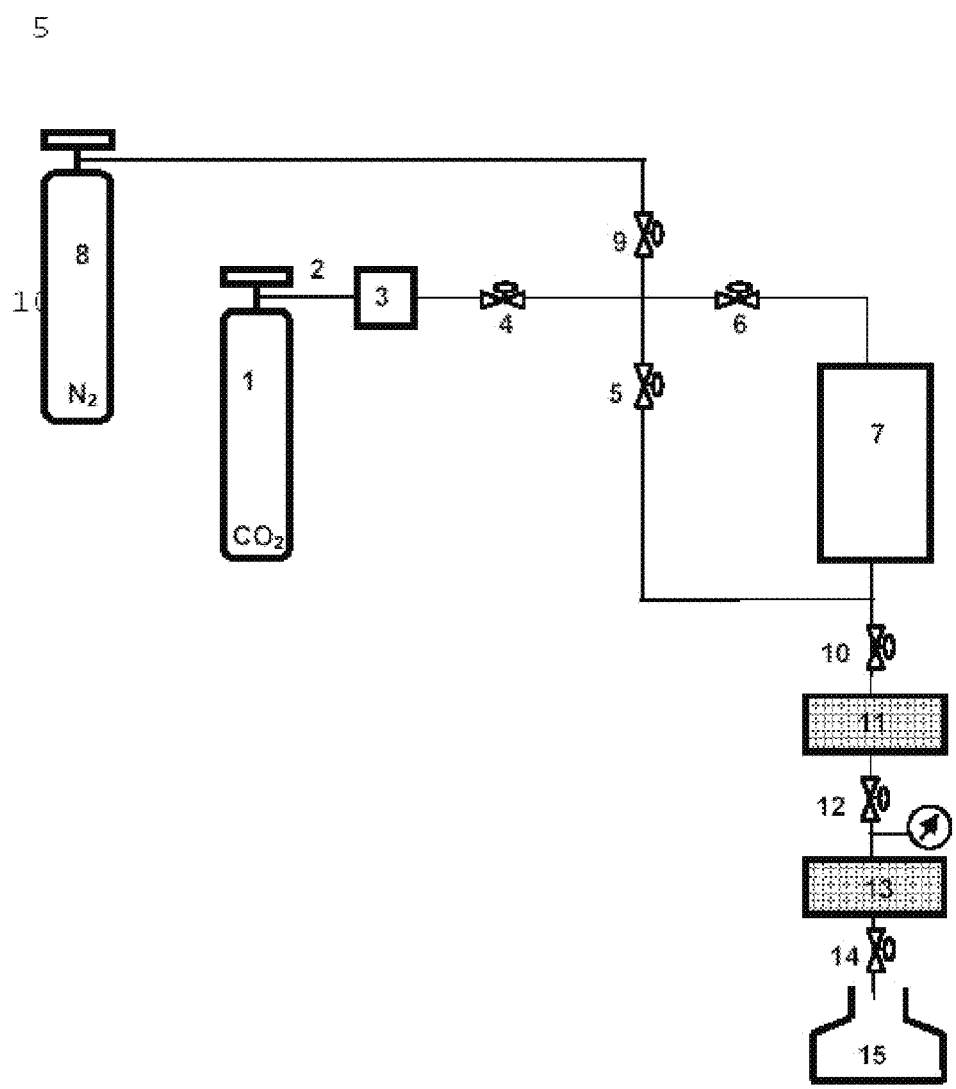

FIG. 2 shows a facility to carry out the process of the invention. Said facility comprises a tank 1 which contains $CO_2$, said tank is connected to a pump 3 to supply said liquid $CO_2$ at high pressure. The adding of liquid $CO_2$ over the mixing reactor 7 where there is already a mixture of organic solvent (or a mixture of organic solvents), a solid compound C and water can be done through the uppermost part through valves 4 and 6, or through valves 4 and 5 through the lower part. Through valves 9 and 5, the addition to the mixing reactor 7 of an inert gas $N_2$, which is in tank 8, is controlled. This inert gas can be used to increase the pressure from $P_1$ to $P_2$ when $\Delta P_{(P2>P1)}>0$. Alternatively, a piston mechanically or pneumatically actuated (not shown) can be used to increase the pressure in mixing reactor 7. The microemulsion formed in reactor 7 at pressure $P_2$ passes to filter 11 through valve 10, where it undergoes the first filtration maintaining the pressure $P_2$. Upon exiting filter 11 and passing through valve 12, the microemulsion containing $CO_2$ is expanded and is rapidly depressurized to atmospheric pressure, with the consequent precipitation of the solid crystalline particles. During the filtration at atmospheric pressure in filter 13, the particles are retained in filter 13 and the mother liquor is collected in container 15 through valve 14.

Figure 3:
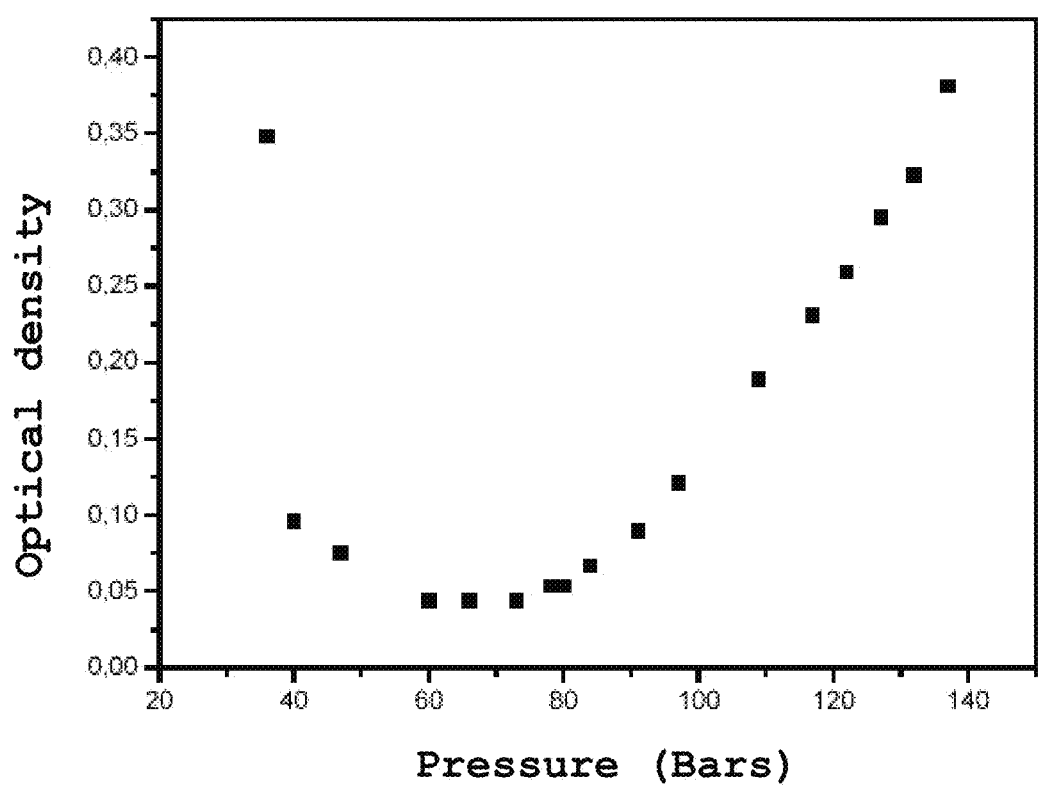

FIG. 3 shows the variation in optic density observed in a microemulsion formed according with the process of the invention, e.g., by the system "ibuprofen/acetone/water/PEG6000/$CO_2$" in function of the pressure at 35° C.

The optical density is defined as the absorbance of an optic element at a determined wavelength and by unit of optical path or distance. The turbidity of a system is defined in terms of optical density when the system does not absorb light at that wavelength.

Figure 4:
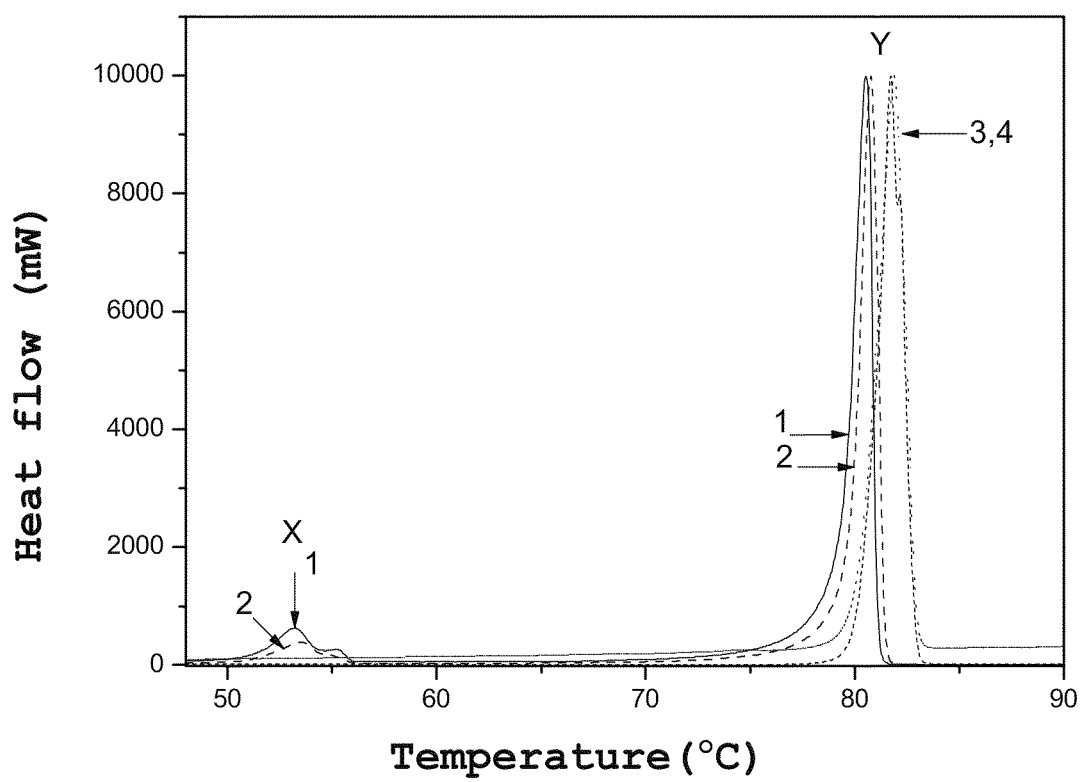

FIG. 4 represents a differential scanning calorimetry profile (DSC) of the solid compound C (ibuprofen) obtained according to the process of the invention, with or without a surfactant (PEG6000). From said figure it can be observed that the presence of the surfactant does not modify the crystalline structure of the solid micro- or nanoparticles nor does it affect it if $\Delta P_{(P2>P1)}<0$ or if $\Delta P_{(P2>P1)}>0$. Profile 1 corresponds to the ibuprofen compound obtained for $\Delta P_{(P2>P1)}>0$ in the presence of surfactant (PEG6000). Profiles 2 and 3 correspond to the ibuprofen compound obtained for $\Delta P_{(P2>P1)}<0$ with or without surfactant (PEG6000), respectively. Profile 4 corresponds to the original unprocessed ibuprofen. In FIG. 4 symbols X and Y correspond to the fusion endothermic peaks of the surfactant (PEG6000) and compound C (ibuprofen), respectively.

Figure 5:
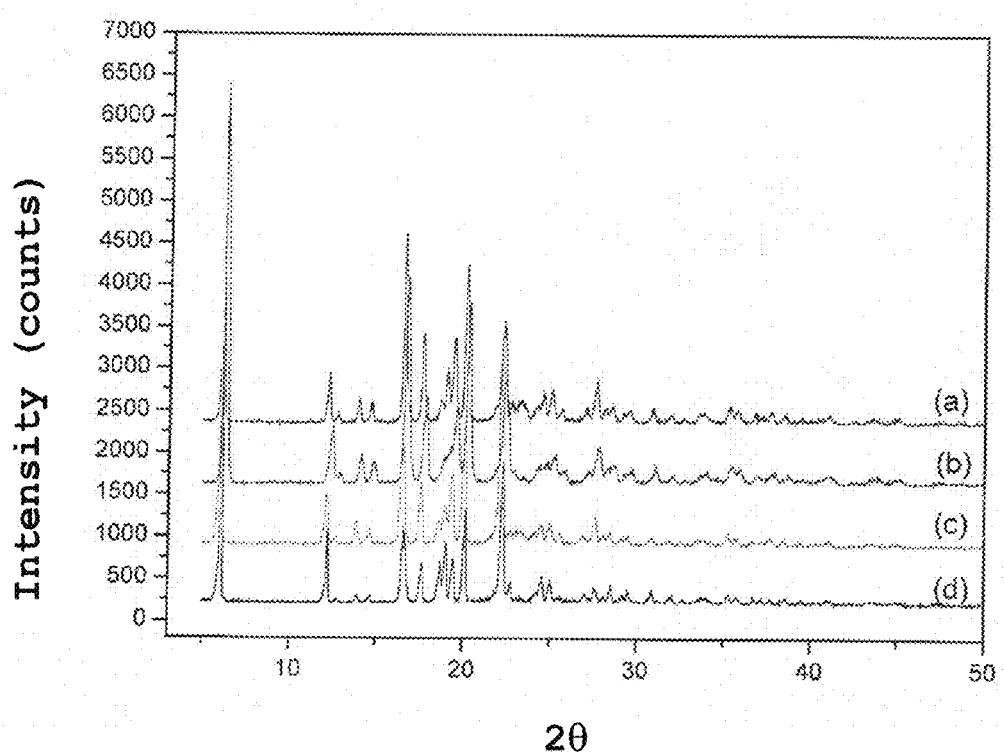

FIG. 5 represents a X-ray diffraction spectrum of solid compound C (ibuprofen) obtained using the process of the invention in presence or absence of surfactant (PEG6000). Particularly, in said figure it can be observed that with the process according to the invention, solid crystalline micro- or nanoparticles are obtained whether $\Delta P_{(P2>P1)}<0$ or $\Delta P_{(P2>P1)}>0$. The spectrums (a) and (b) correspond to the ibuprofen compound obtained for $\Delta P_{(P2>P1)}<0$ with or without surfactant (PEG6000), respectively. Spectrum (c) corresponds to the ibuprofen compound obtained for $\Delta P_{(P2>P1)}>0$ with surfactant (PEG6000). Spectrum (d) corresponds to the original unprocessed ibuprofen compound.

Figure 6A:
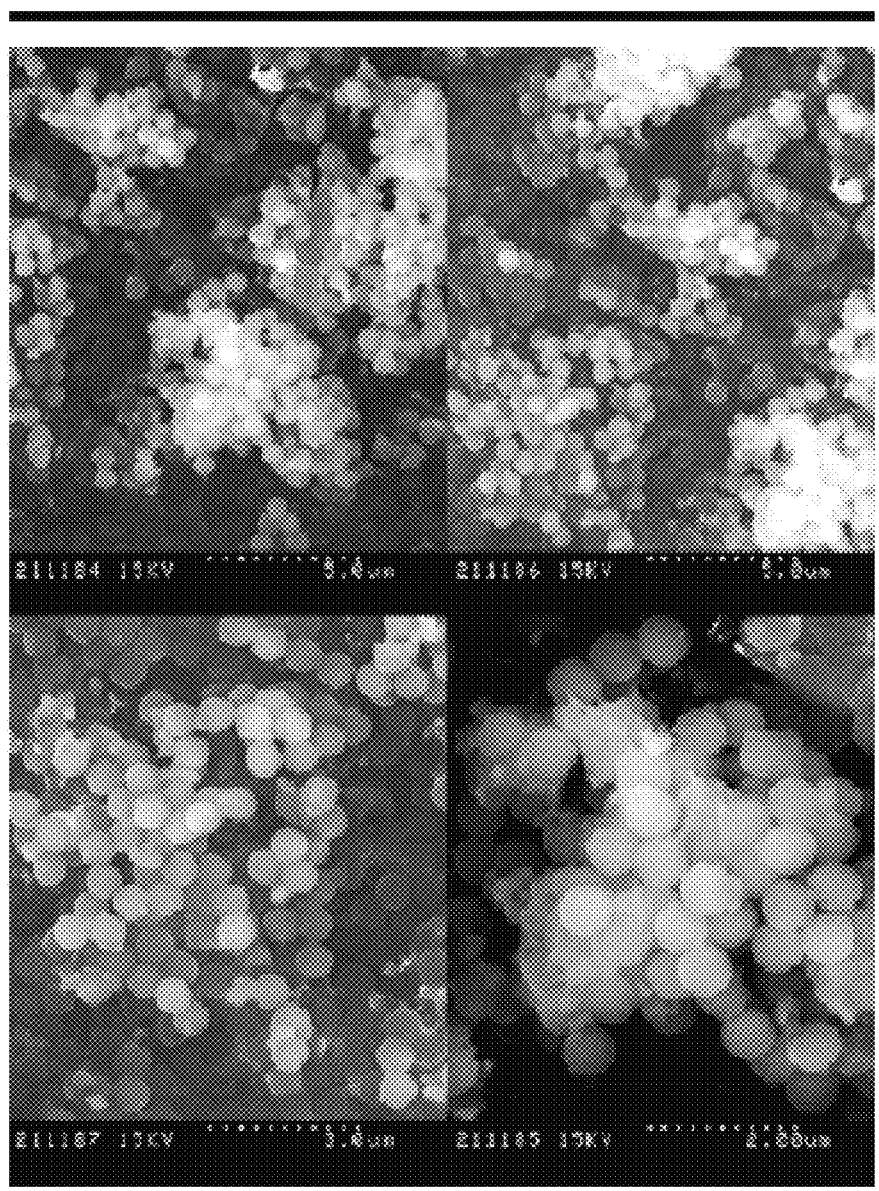

FIG. 6A is an image of a scanning electron microscope (SEM) of the ibuprofen compound obtained without surfactant and $\Delta P<0$ (P2<P1).

Ibuprofen/acetone/water/$CO_2$, without surfactant;
Precipitation obtained at $P_2$=atmospheric pressure
$X_{CO2}$=0,16 (molar fraction of $CO_2$);
Solid collected in a non-pressurized filter;
Average diameter of particle: 740 nm;
Total output of the solid collected: 86%.

Figure 6B:
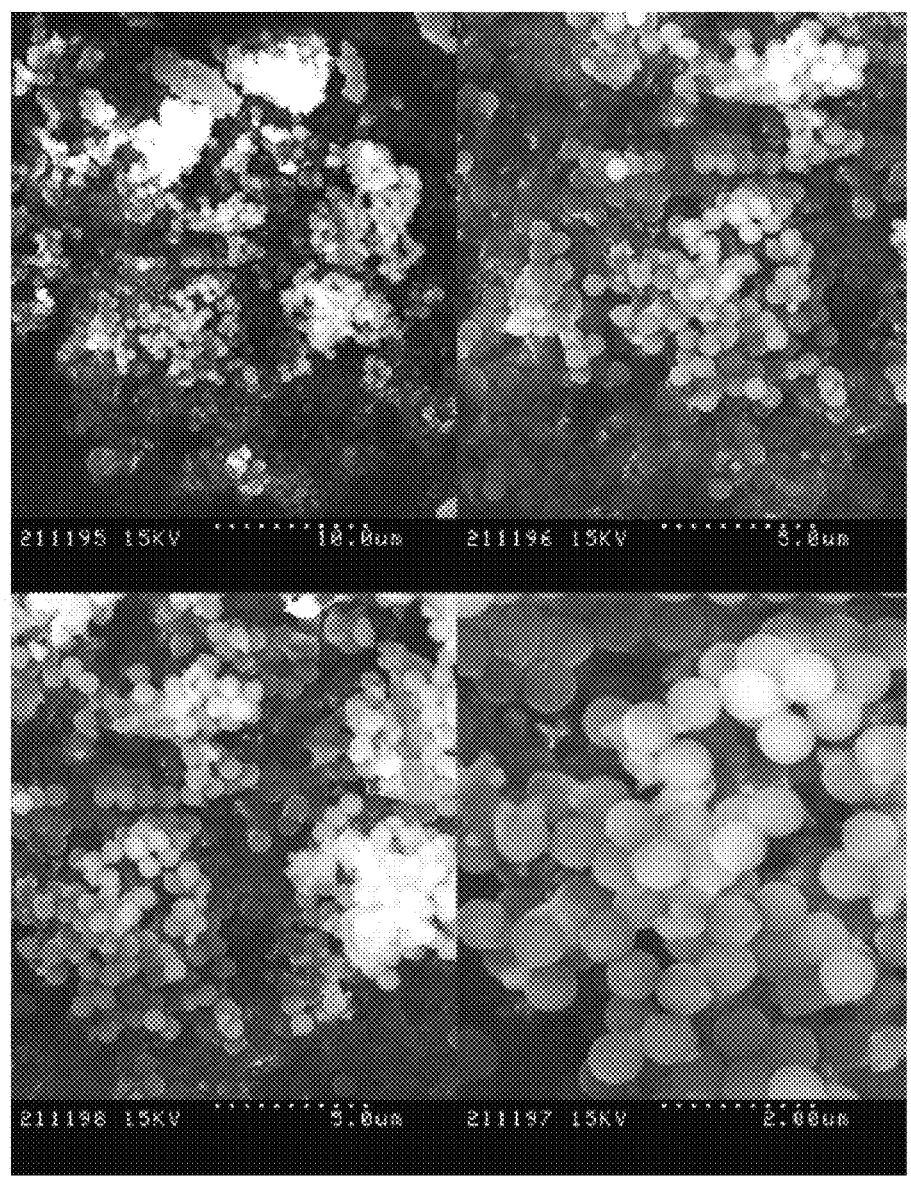

FIG. 6B is an image of a scanning electron microscope (SEM) of the ibuprofen compound obtained with PEG6000 and $\Delta P<0$ (P2<P1).

Ibuprofen/acetone/water/$CO_2$/PEG6000;
Precipitation obtained at $P_2$=atmospheric pressure
$X_{CO2}$=0,16 (molar fraction of $CO_2$);
Solid collected in a non-pressurized filter;
Average diameter of particle: 680 nm;
Total output of the solid collected: 81%.

From comparing FIGS. 6A and 6B it can be observed that with $\Delta P<0$ the presence of the surfactant influences the size of the particle, reducing it with its presence.

Figure 6C:
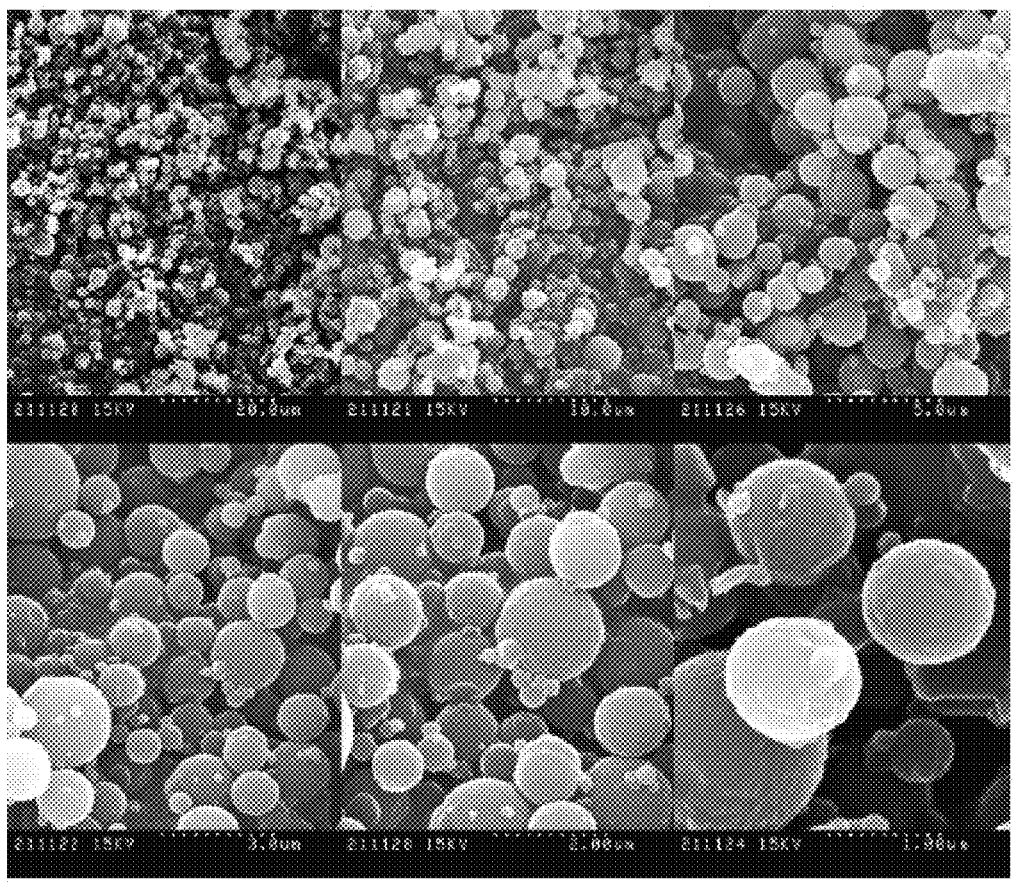

FIG. 6C is an image of a scanning electron microscope (SEM) of the ibuprofen compound obtained with PEG6000 and $\Delta P>0$ (P2>P1).

Ibuprofen/acetone/water/$CO_2$/PEG6000;
Precipitation obtained at P2=147 bars and 35° C.;
$X_{CO2}$=0,16 (molar fraction of $CO_2$);
Solid collected in a non-pressurized filter;
Average diameter of particle: 935 nm;

Below, preferred embodiments of this invention are described, without limiting.

EXAMPLES

Example 1

Obtaining Nanoparticles of Ibuprofen Through the Process of the Invention when $\Delta P<0$ (without Surfactant)

In a mixing reactor 7 of 300 mL capacity, 170 mL of a solution of the ibuprofen compound in acetone with a relative concentration to saturation of 63% and 90 mL of $H_2O$, obtaining a suspension of the drug in the acetone-water mixture. Over this suspension $CO_2$ is added with a volume of flow of 7 Kg/hr until the pressure $P_1$ of reactor 7 reaches the 100 Bar. The temperature is kept constant throughout the entire process at 35° C. At these conditions, this system is formed by a transparent microemulsion consisting of the system ibuprofen/acetone/water/$CO_2$. The microemulsion is left to stabilize at P1 and 35° C. during 15 minutes (see FIG. 2). The supply of $CO_2$ is closed and the adding of $N_2$ begins through the uppermost part of the reactor through valve 6, to maintain the pressure P1 constant at 100 bar within the reactor during the depressurization process of the microemulsion. The depressurization of the microemulsion from P1 to P2=1 bar, with the consequent rapid evaporation of $CO_2$, is done through the opening of a valve 12. The evaporation of $CO_2$ causes the water to again manifest its new anti-solvent characteristic over the dissolved ibuprofen in the organic phase, causing its precipitation. The precipitated particles are collected in filter 13 at P2=1 bar (atmospheric pressure). The precipitated particles are washed with $CO_2$ at 40 Bar. The mother liquors are collected in container 15 through valve 14. The size of the particle of the ibuprofen compound was determined through a scanning electron microscope (SEM). The distribution of particle sizes of the collected solid phase in filter 13 have an average of 740 nm with a standard deviation of 100 nm. It was observed through X-ray powder diffraction that the particles obtained are crystalline, and by using the scanning electron microscope (SEM) that they have a homogenous spheroidal morphology (see FIG. 5A). The output of the process is of 86%.

Optionally, there is a second filter to collect the possible solids that did not dissolve in the microemulsion obtained at pressure P1; said filter is represented in FIG. 2 as filter 11.

Example 2

Obtaining Nanoparticles of Ibuprofen Through the Process of the Invention when ΔP<0 (in Presence of a Surfactant PEG6000 Dissolved in the Aqueous Phase)

In a mixing reactor 7 of 300 mL capacity, 170 mL of a solution of the ibuprofen compound in acetone with a relative concentration of 63% and 90 mL of an aqueous solution which contains 10% in weight of the surfactant PEG6000, are introduced, obtaining a suspension of the drug in the acetone-water mixture. Over this suspension $CO_2$ is added with a volume of flow of 7 Kg/hr until the pressure P1 of reactor 7 reaches 100 bar. The temperature is kept constant throughout the entire process at 35° C. At these conditions, this system is formed by a transparent microemulsion consisting of the system ibuprofen/acetone/water/PEG6000/$CO_2$. The microemulsion is left to stabilize at P1 and 35° C. during 15 minutes (see FIG. 2). The supply of $CO_2$ is closed and the adding of $N_2$ begins through the uppermost part of the reactor 7 through valve 6, to maintain the pressure P1 constant at 100 Bars within the reactor during the depressurization process of the microemulsion. The depressurization of the microemulsion from P1 to P2=1 Bar, with the consequent rapid evaporation of $CO_2$, is done through the opening of a valve 12. The evaporation of $CO_2$ causes the water to again manifest its new anti-solvent characteristic over the dissolved ibuprofen in the organic phase, causing its precipitation. The precipitated particles are collected in filter 13 at P2=1 bar (atmospheric pressure). The precipitated particles are washed with $CO_2$ at 40 Bar. The mother liquors are collected in container 15 through valve 14. The size of the particle of the ibuprofen compound was determined through a scanning electron microscope (SEM). The distribution of particle sizes of the collected solid phase in filter 13 have an average of 680 nm with a standard deviation of 110 nm. It was observed through X-ray powder diffraction that the particles obtained are crystalline, and by using the scanning electron microscope (SEM) that they have a homogenous spheroidal morphology (see FIG. 5B). The output of the process is of 81%.

Optionally, there is a second filter to collect the possible solids that did not dissolve in the microemulsion obtained at pressure P1; said filter is represented in FIG. 2 as filter 11.

Example 3

Obtaining Nanoparticles of Ibuprofen Through the Process of the Invention when ΔP>0 (without Surfactant)

In a mixing reactor 7 of 300 mL capacity, 170 mL of a solution of the ibuprofen compound in acetone with a relative concentration of 63% and 90 mL of $H_2O$ are introduced, obtaining a suspension of the drug in the acetone-water mixture. Over this suspension $CO_2$ is added with a volume of flow of 7 Kg/hr until the pressure P1 of reactor 7 reaches 100 bar. The temperature is kept constant throughout the entire process at 35° C. At these conditions, this system is formed by a transparent microemulsion consisting of the system ibuprofen/acetone/water/$CO_2$. The microemulsion is left to stabilize at P1 and 35° C. during 15 minutes (see FIG. 2). The supply of $CO_2$ is closed and the adding of $N_2$ begins through the uppermost part of the reactor 7 through valve 6, until a pressure P2=146 Bar within the reactor (P2>P1) is reached. The increase in pressure from P1 to P2 stimulates the water to again manifest its new anti-solvent effect over the solute present in the system solute/organic solvent/water/$CO_2$, causing its precipitation. The precipitated solid is filtered over filter 11 at pressure P2. The precipitation of the mother liquors is done through valve 12 and they are collected in tank 15, after passing through filter 13 and valve 14. The solid collected in filter 11 is washed with $CO_2$ at 40 Bar. The size of the particle of the ibuprofen compound was determined through a scanning electron microscope (SEM). The distribution of particle sizes of the collected solid phase in filter 11 have an average of 940 nm with a standard deviation of 300 nm. It was observed through X-ray powder diffraction that the particles obtained are crystalline, and by using the scanning electron microscope (SEM) that they have a homogenous spheroidal morphology. The output of the process is of 20%.

Example 4

Obtaining Nanoparticles of Ibuprofen Through the Process of the Invention when ΔP>0 (in Presence of a Surfactant PEG6000 Dissolved in the Aqueous Phase)

In a mixing reactor 7 of 300 mL capacity, 170 mL of a solution of the ibuprofen compound in acetone with a relative concentration of 63% and 90 mL of an aqueous solution which contains 10% in weight of surfactant PEG6000, are introduced, obtaining a suspension of the drug in the acetone-water mixture. Over this suspension $CO_2$ is added with a volume of flow of 7 Kg/hr until the pressure P1 of reactor 7 reaches 100 bar. The temperature is kept constant throughout the entire process at 35° C. At these conditions, this system is formed by a transparent microemulsion consisting of the system ibuprofen/acetone/water/PEG6000/$CO_2$. The microemulsion is left to stabilize at P1 and 35° C. during 15 minutes (see FIG. 2). The supply of $CO_2$ is closed and the adding of $N_2$ begins through the uppermost part of the reactor 7 through valve 6 until a pressure $P_2$=146 Bar within the reactor (P2>P1) is reached. The increase in pressure from P1 to P2 stimulates the water to again manifest its new anti-solvent effect over the solute present in the system solute/organic solvent/water/PEG6000/$CO_2$, causing its precipitation. The precipitated solid is filtered over filter 11 at pressure P2. The precipitation of the mother liquors is done through valve 12 and they are collected in tank 15, after passing through filter 13 and valve 14. The solid collected in filter 11 is washed with $CO_2$ at 40 Bar. The size of the particle of the ibuprofen compound was determined through a scanning electron microscope (SEM). The distribution of particle sizes of the collected solid phase in filter 11 have an average of 935 nm with a standard deviation of 460 nm. It was observed through X-ray powder diffraction that the particles obtained are crystalline, and by using the scanning electron microscope (SEM) that they have a homogenous spheroidal morphology. The output of the process is of 21%. (See FIG. 6C)

The invention claimed is:

1. A method for obtaining solid micro- or nanoparticles which comprises the steps of:
   a) preparing in a closed container a mixture that includes an organic solvent or a mixture of organic solvents, a solid compound C and water,
   where in step a) there is at least one liquid phase and one solid phase,
   b) adding a fluid B to said mixture prepared in step a) so that the container reaches a first pressure $P_1$, allowing said addition of fluid B at said first pressure, $P_1$, to prepare a microemulsion of an organic phase saturated with water,
   where there is no solid phase in step b) and where at said first pressure, $P_1$, a predetermined supersaturation value, β, of the solid compound C is less than or equal to 1,
   wherein said fluid B is a fluid which at atmospheric pressure and room temperature is a gas and which at said first pressure, $P_1$, greater than atmospheric pressure, is miscible with the organic solvent, and immiscible or partially miscible with water, and is not a supercritical fluid at any stage,
   c) varying said first pressure, $P_1$, to a second pressure, $P_2$, where said variation in pressure does not equal zero, and where at said second pressure, $P_2$, said water has an anti-solvent effect which causes precipitation of solid micro- or nanoparticles of compound C with homogenous structure;
   where in step c) there is at least one liquid phase and one solid phase;
   and, optionally;
   d) collecting at said second pressure, P2, said solid micro- or nanoparticles by conventional methods,
   wherein said solid micro- or nanoparticles have an aspect ratio value close to unity (1).

2. The method according to claim 1, wherein said steps a) and b) are carried out simultaneously.

3. The method according to claim 1, wherein in step a) the mixture includes a surfactant.

4. The method according to claim 1, wherein in step a) said container is at atmospheric pressure and room temperature.

5. The method according to claim 1, wherein in step c) said variation is such that the second pressure, $P_2$, is greater than the first pressure, $P_1$.

6. The method according to claim 5, wherein said step c) is reversible such that precipitation is a reversible phenomenon.

7. The method according to claim 1, wherein in step c) said variation is such that the second pressure, $P_2$, is lower than the first pressure, $P_1$.

8. The method according to claim 1, wherein when the second pressure, P2, is greater than the first pressure, P1, said organic solvent is a polar or non-polar solvent.

9. The method according to claim 1, wherein when the second pressure, P2, is lower than the first pressure, P1, said organic solvent is a polar solvent.

10. The method according to claim 1, wherein said solid compound C is insoluble or partially insoluble in said $H_2O$.

11. The method according to claim 1, wherein said fluid B is $CO_2$.

12. The method according to claim 1, wherein said solid micro- or nanoparticles have a particle size of less than 10 μm.

13. The method according to claim 1, wherein said micro- or nanoparticles have a substantially spheroidal morphology.

14. The method according to claim 1, wherein solid compound C has a crystalline nature and said micro- or nanoparticles obtained therefrom have a crystalline structure.

15. A composition which comprises solid micro- or nanoparticles obtained according to claim 1 together with acceptable pharmaceutical excipients.

16. A medicine for oral administration in aerosol form comprising solid micro- or nanoparticles obtained according to claim 1.

17. A suspension for oral, intravenous, or mucosal administration comprising solid micro- or nanoparticles obtained according to claim 1.

* * * * *